(12) United States Patent
Acevedo et al.

(10) Patent No.: US 6,861,577 B2
(45) Date of Patent: Mar. 1, 2005

(54) PROMOTER OF A MAIZE MAJOR LATEX PROTEIN GENE AND METHODS OF USING IT TO EXPRESS HETEROLOGOUS NUCLEIC ACIDS IN TRANSFORMED PLANTS

(75) Inventors: Pedro A. Navarro Acevedo, Ames, IA (US); Carl R. Simmons, Des Moines, IA (US); John T. Tossberg, Durham, NC (US); Nasser Yalpani, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 226 days.

(21) Appl. No.: 09/945,376

(22) Filed: Aug. 31, 2001

(65) Prior Publication Data

US 2002/0083493 A1 Jun. 27, 2002

Related U.S. Application Data

(60) Provisional application No. 60/231,418, filed on Sep. 5, 2000.

(51) Int. Cl.[7] ............................ A01H 5/00; A01H 5/10; C12N 15/82; C12N 15/11; C12N 5/04
(52) U.S. Cl. .................... 800/298; 800/320.1; 800/278; 435/419; 435/412; 536/24.1
(58) Field of Search ...................... 536/24.1; 435/320.1, 435/468, 419, 430, 412; 800/278, 298, 320.1

(56) References Cited

U.S. PATENT DOCUMENTS 6,462,257 B1 * 10/2002 Perera et al. ............... 800/287

FOREIGN PATENT DOCUMENTS

WO    WO 98/30698    * 7/1998

OTHER PUBLICATIONS

Kim et al, 1994, Plant Mol. Biol. 24:105–117.*
Donald et al, 1990, EMBO J. 9:1717–1726.*
Gordon–Kamm et al, 1990, Plant Cell 2:603–618.*
Maiti et al, 1997, Transgen. Res., 6:143–156.*
Doelling et al, 1995, Plant J. 8:683–692.*
Chen et al, 2000, Sex. Plant Reprod. 13:85–94.*
Benfrey et al, 1990, Science 250:959–966.*
Aggelis, A., et al., "Characterization of two cDNA Clones for mRNAs Expressed During Ripening of Melon (*Cucumis melo* L. ) Fruits," *Plant Molocular Biology*, 1997, pp. 313–322, vol. 33, Kluwer Academic Publishers, Belgium.

Nam, Y–O, et al., "Isolation and Characterization of mRNAs Differentially Expressed During Ripening of Wild Strawberry (*Fragaric vesco* L) Fruits," *Plant Molecular Biology*, 1999, pp. 629–636, vol. 39, Kluwer Academic Publishers, Netherlands.

Nessler, C.L. et al., "Isosation and Analysis of the Major Latex Protein Genes of Opium Poppy." *Plant Molecular Biology*, 1990, pp. 951–953, vol. 15, Kluwer Academic Publishers, Belgium.

Nessler, C.L., and R.J. Burnett, "Organization of the Major Latex Protein Gene Family in Opium Poppy," *Plant Molecular Biology*, 1992, pp. 749–752, vol. 20, Kluwer Academic Publishers, Belgium.

Nessler, C.L., Sequence Analysis of two new Members of the Major Latex Protein Gene Family Supports the Triploid–Hybrid Origin of the Opium Poppy, Gene, 1994, pp. 207–209, vol. 139, Elsevier Science B.V.

* cited by examiner

*Primary Examiner*—Anne Kubelik
(74) *Attorney, Agent, or Firm*—Pioneer Hi-Bred International, Inc.

(57) ABSTRACT

Compositions and methods to aid in protecting plants from invading pathogenic organisms are provided. The compositions of the invention comprise an anti-pathogenic gene, including the promoter driving expression of the gene, and the protein encoded by the anti-pathogenic gene. The compositions find use in methods for reducing or eliminating damage to plants caused by plant pathogens. Transformed plants, plant cells, tissues, and seed are also provided having enhanced disease resistance.

17 Claims, 1 Drawing Sheet

PROMOTER OF A MAIZE MAJOR LATEX PROTEIN GENE AND METHODS OF USING IT TO EXPRESS HETEROLOGOUS NUCLEIC ACIDS IN TRANSFORMED PLANTS

CROSS-REFERENCE TO RELATED APPLICATIONS

This application claims priority to and benefit of U.S. Provisional Patent Application Serial No. 60/231,418, filed on Sep. 5, 2000, which is incorporated herein by reference in its entirety.

FIELD OF THE INVENTION

The invention relates to nucleotide sequences and proteins for anti-pathogenic agents and their uses, particularly the genetic manipulation of plants with genes and promoters that enhance disease resistance.

BACKGROUND OF THE INVENTION

Among the causal agents of infectious diseases of crop plants, phytopathogenic fungi play the dominant role, not only by causing devastating epidemics, but also through the less spectacular although persistent and significant annual crop yield losses that have made fungal pathogens a serious economic factor. All flowering plant species are attacked by pathogenic fungi. To colonize plants, fungal microorganisms have evolved strategies to invade plant tissue, to optimize growth in the plant, and to propagate. Bacteria and viruses, as well as some opportunistic fungal parasites, often depend on natural openings or wounds for invasion. In contrast, many true phytopathogenic fungi have evolved mechanisms to actively traverse the plants' outer structural barriers, the cuticle and the epidermal cell wall. To gain entrance, fungi generally secrete a cocktail of hydrolytic enzymes.

Despite the large number of microorganisms capable of causing disease, most plants are resistant to any given pathogen. The defense mechanisms utilized by plants can take many different forms, ranging from passive mechanical or preformed chemical barriers that provide non-specific protection against a wide range of organisms to more active host-specific responses that provide host- or varietal-specific resistance.

A hypersensitive response (HR) that is elaborated in response to invasion by all classes of pathogens is the most common feature associated with active host resistance. In most cases, activation of the HR leads to the death of cells at the infection site, which results in the restriction of the pathogen to small areas immediately surrounding the initially infected cells. At the whole-plant level, the HR is manifested as small necrotic lesions. The number of cells affected by the HR is only a small fraction of the total in the plant, so this response obviously contributes to the survival of plants undergoing pathogen attack.

In plants, robust defense responses to invading phytopathogens often conform to a gene-for-gene relationship. Resistance to a pathogen is only observed when the pathogen carries a specific avirulence (avr) gene and the plant carries a corresponding resistance (R) gene. Because avr-R gene-for-gene relationships are observed in many plant-pathogen systems and are accompanied by a characteristic set of defense responses, a common molecular mechanism underlying avr-R gene-mediated resistance has been postulated. Thus, disease resistance results from the expression of a resistance gene in the plant and a corresponding avirulence gene in the pathogen and is often associated with the rapid, localized cell death characteristic of the hypersensitive response. R genes that respond to specific bacteria, fungal, or viral pathogens have been isolated from a variety of plant species and several appear to encode cytoplasmic proteins.

The development of new strategies to control diseases is the primary purpose of research on plant-pathogen interactions. These include, for example, the identification of essential pathogen virulence factors and the development of means to block them, or the transfer of resistance genes into crop plants from unrelated species. An additional benefit is a better understanding of the physiology of the healthy plant through a study of the metabolic disturbances caused by plant pathogens.

SUMMARY OF THE INVENTION

Anti-pathogenic compositions and methods for their use are provided. The compositions comprise anti-pathogenic proteins and their corresponding gene sequences and regulatory regions. Particularly, a maize major latex protein, as well as fragments and variants thereof, are provided.

The compositions and methods are useful in protecting plants from invading pathogenic organisms. One method involves stably transforming a plant with nucleotide sequences of the invention to engineer broad-spectrum disease resistance in the plant and to provide protection from stresses, including pathogen attack, wounding, abiotic stresses (such as, for example, heat, drought, cold, reactive oxygen species, radiation, etc.), and the like. The nucleotide sequences are expressed from a promoter capable of driving expression in a plant cell. Another method involves controlling plant pathogens by applying an effective amount of an anti-pathogenic protein or composition to the plant environment. Additionally, the nucleotide sequences of the invention are useful as genetic markers in disease-resistance breeding programs.

Promoters of the invention find use as pathogen-inducible promoters. Such promoters may be used to express other coding regions, particularly other anti-pathogenic genes, such as disease- and insect-resistance genes.

The compositions of the invention additionally find use in agricultural and pharmaceutical compositions as antifungal and antimicrobial agents. For agricultural purposes, the compositions may be used in sprays for control of plant disease. As pharmaceutical compositions, the agents are useful as antibacterial and antimicrobial treatments.

Thus, the compositions and methods of the invention find use in controlling pests, including fungal pathogens, viruses, nematodes, insects, and the like. Transformed plants, plant cells, plant tissues, and seeds, as well as methods for producing the same, are additionally provided.

DETAILED DESCRIPTION OF THE INVENTION

Definitions

Figure 1:
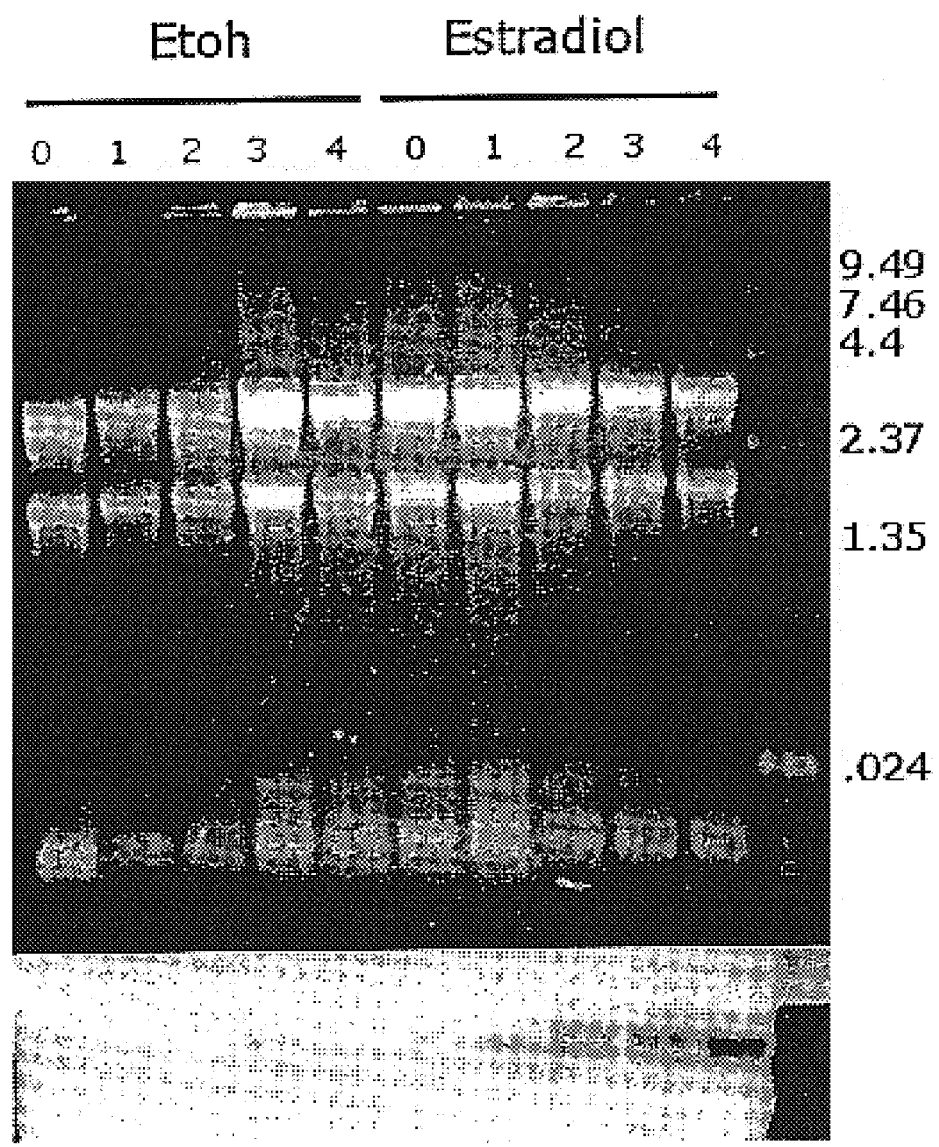
FIG. 1 shows an RNA gel and Northern blot analysis of RNA samples taken from maize suspension cultures transformed with the PHP12242 (ERE::AvrRxv) construct. This construct places the transcription of an avrRxv nucleotide sequence under control of the estrogen receptor. Treatment of these transgenic suspension cultures with estradiol induces expression of the avrRxv gene and the disease response pathway. The RNA gel is stained with ethidium bromide to demonstrate the equality of gel loading, and the position of molecular weight markers (in kilobases) is indicated on the right-hand side of the gel. The Northern blot assay (probed with a major latex gene probe) is shown below. The control treatment (with ethanol, "Etoh") is shown in the left-hand set of lanes and shows no induction of transcription of the major latex protein gene. In contrast, treatment with estradiol induced expression of the major latex protein, indicating that expression of the major latex protein (Zm-MLP1) is part of the plant disease response.

By "agronomic trait" is intended a phenotypic trait of an agricultural plant that contributes to the performance or economic value of the plant. Such traits include, for example, disease resistance, insect resistance, nematode resistance, virus resistance, drought tolerance, high salinity tolerance, yield, plant height, days to maturity, seed nitrogen content, seed oil content, seed or fruit color, seed or fruit size, and the like.

By "anti-pathogenic compositions" is intended that the compositions of the invention have anti-pathogenic activity and thus are capable of suppressing, controlling, and/or killing the invading pathogenic organism. Such anti-pathogenic compositions of the invention include an isolated maize major latex gene, its promoter region, and the protein encoded by the gene, as well as nucleotide and amino acid sequence fragments and variants thereof that retain their biological or regulatory function. The compositions find use in protecting plants against fungal pathogens, viruses, nematodes, insects, and the like by way of enhancing plant disease resistance. Additionally, the compositions can be used in formulations for their antibacterial and antimicrobial activities.

By "antisense DNA nucleotide sequence" is intended a sequence that is complementary to at least a portion of the messenger RNA (mRNA) for a targeted gene sequence.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen are minimized or lessened. The methods of the invention can be utilized to protect plants from disease, particularly those diseases that are caused by plant pathogens.

By "foreign" is intended that the transcriptional initiation region is not normally found in the native plant into which the transcriptional initiation region is introduced. As used herein, a chimeric gene comprises a coding sequence operably linked to a transcription initiation region that is heterogolous to the coding sequence.

By "fragment" is intended a portion of the nucleotide sequence or a portion of the amino acid sequence, and hence the protein encoded thereby. Fragments of a nucleotide sequence may encode protein fragments that retain the anti-pathogenic biological activity of the native protein, and hence provide disease resistance. Alternatively, fragments of a nucleotide sequence that are useful as hybridization probes, such as described elsewhere herein, generally do not encode protein fragments that retain this biological activity. Fragments of a regulatory sequence disclosed herein might retain their regulatory activity; for example, fragments of a promoter may retain their promoter activity.

By "inducible promoter" is intended that the promoter initiates expression of a gene in the presence of a pathogen or chemical stimulus. Similarly, by "inducible expression" is intended that transcription of the coding sequence and subsequent translation of the messenger RNA are initiated in response to the presence of a pathogen or chemical stimulus to produce an anti-pathogenic protein.

When using an inducible promoter, expression of the nucleotide sequence is initiated in cells in response to a stimulus. By "stimulus" is intended a chemical or environmental stimulus which may be applied externally or may accumulate in response to another external stimulus. For example, a pathogen may induce expression by attempting to invade or by invading a plant cell. Other stimuli can include environmental stresses, including but not limited to drought, temperature, and salinity.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

By "nucleic acid molecule" or "nucleic acid" (terms used interchangeably herein) is intended a molecule composed of nucleotides covalently bound to one another. Nucleotides include both ribonucleotides and deoxyribonucleotides. "Nucleic acid molecule" encompasses single-stranded and double stranded forms of both DNA and RNA. Nucleic acid molecules may be naturally occurring, synthetic, or a combination of both. The linear arrangement of nucleotides in a nucleic acid molecule is referred to as a "nucleotide sequence" and, unless specified otherwise, is presented herein from left to right corresponding to the 5'-to-3' direction.

By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

By "pathogenic agent" or "pathogen" is intended any organism that has the potential to negatively impact a plant, typically, but not exclusively, by causing disease or inflicting physical damage. Such organisms include, but are not limited to, fungi, bacteria, nematodes, mycoplasmas, viruses, and insects.

By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream ("5'") to the TATA box, referred to as upstream promoter elements, which influence the transcription initiation rate.

By "stably transformed" is intended that the nucleotide sequences introduced into a cell and/or plant using transformation methods described herein are stably incorporated into the genome of the cell and/or plant. Stably incorporated nucleotide sequences are heritable.

By "variants" is intended substantially similar sequences. For nucleotide sequences, conservative variants include those sequences that, because of the degeneracy of the genetic code, encode the amino acid sequence of one of the anti-pathogenic protein of the invention. Naturally-occurring allelic variants such as these can be identified with the use of well-known molecular biology techniques, as, for example, with polymerase chain reaction (PCR) and hybridization techniques as outlined below. Variant nucleotide sequences also include synthetically-derived nucleotide sequences, such as those generated, for example, by using site-directed mutagenesis or DNA shuffling as described elsewhere herein, but which still encode an anti-pathogenic protein of the invention, or, in the case of variants of a promoter sequence, retain promoter activity. Generally, variants of a particular nucleotide sequence of the invention will have at least 40%, 50%, 60%, 65%, 70%, generally at least 75%, 80%, 85%, preferably about 90%, 91%, 92%, 93%, 94%, 95%, and more preferably about 96%, 97%, 98%, 99% or more sequence identity to that particular nucleotide sequence as determined by sequence alignment programs described elsewhere herein using default parameters.

By "variant protein" is intended a protein derived from the native protein by deletion (so-called "truncation") or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention will continue to possess the desired biological activity of the native protein, that is, anti-pathogenic activity as described herein. Such variants may result from, for example, genetic polymorphism or from human manipulation. Biologically active variants of a native anti-pathogenic protein of the invention will have at least 40%, 50%, 60%, 65%, 70%, generally at least 75%, 80%, 85%, preferably about 90%, 91%, 92%, 93%, 94%, 95% or more, and more preferably about 96%, 97%, 98%, 99% or more sequence identity to the amino acid sequence for the native protein as determined by sequence alignment programs described elsewhere herein using default parameters. A biologically active variant of a protein of the invention may differ from that protein by as few as 15 amino acid residues, as few as 12, as few as 10, 9, 8, 7, 6, as few as 5, or as few as 4, 3, 2, or even 1 amino acid residue.

By "stringent conditions" or "stringent hybridization conditions" is intended conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl Anal. Biochem. 138: 267–284(1984): $T_m$=81.5° C.+16.6 (log M)+0.41(%GC)–0.61(% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to allow hybridization of sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A*

*Laboratory Manual* (2d ed., Cold Spring Harbor Laboratory Press, Plainview, N.Y.).

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244; Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988), supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, and/or PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95% identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Introduction

A novel defense-induced maize gene and the promoter driving expression of the gene are provided. The gene is a maize major latex gene, designated Zm-MLP1. The gene is upregulated, even within an hour of defense activation. The sequences are useful for enhancing disease resistance or tolerance, for example, by expression of the coding region. In another embodiment, the promoter region may be used to drive inducible expression of this or other genes for combating pathogens directly or indirectly through the activation of general maize defense response. The Zm-MLP1 gene belongs to a class of plant proteins that are variously described as major latex proteins or intracellular PR proteins or root allergen proteins. While their biochemical role has not been described, they function to allow the plant cells to tolerate stress. The previously published members of the gene family have been from dicotyledonous species.

Nucleotide and Amino Acid Sequences

Compositions and methods for controlling pathogenic agents are provided. The compositions comprise a maize gene, including its promoter, and the anti-pathogenic protein encoded by this gene. Methods of the invention utilize these anti-pathogenic compositions to protect plants against fungal pathogens, viruses, nematodes, insects, and the like. Additionally, the compositions can be used in formulations for their antibacterial and antimicrobial activities.

In particular, the present invention provides isolated nucleic acid molecules comprising the nucleotide sequence set forth in SEQ ID NO:1, nucleotide sequences encoding the amino acid sequence set forth in SEQ ID NO:2, and the nucleotide sequences for the plant promoter set forth in SEQ ID NO:3. Further provided are polypeptides having an amino acid sequence set forth in SEQ ID NO:2 and those encoded by a nucleic acid molecule described herein, for example the coding sequence set forth in SEQ ID NO:1, and fragments and variants thereof. In addition, polypeptides are provided having an amino acid sequence as set forth in SEQ ID NO:2 as well as polypeptides encoded by a nucleotide sequence set forth in SEQ ID NO:1.

Zm-MLP1 contains 835 nucleotides (nt) including a polyA tail. The polyA tail is 18 nt in length (nt 818–835); the length exclusive of the polyA tail is 817 nt. A 5' nontranslated leader is present at nt 1–77 with the coding region (nt 78–542) encoding 154 amino acids. The gene comprises a 3' nontranslated leader at nt 543–817. There is a well-defined polyA adenylation signal of "AATAAA" at −39 to −34 from the polyA adenylation signal.

Fragments and variants of the disclosed nucleotide sequences and proteins encoded thereby are also encompassed by the present invention. By "fragment" is intended a portion of the nucleotide sequence or a portion of the amino acid sequence and hence polypeptide encoded thereby if the nucleotide sequence encodes a polypeptide. Fragments of a nucleotide sequence retain the biological activity of the native sequence and hence are capable of initiating transcription in a plant. Alternatively, fragments of a nucleotide sequence that are useful as hybridization probes generally do not encode fragment proteins retaining biological activity. Thus, fragments of a nucleotide sequence may range from at least about 20, 30, 40, 50, 60, 70, 80, 90, 100, 150, 200, 250, 300, 350, 400, 450, 500, 550, 600, 650, 700, 750, 800, 850, 900, 950, 1000 nucleotides, and up to the full length nucleotide sequence (1030 nucleotides) of SEQ ID NO:3.

The sequences of the invention find use as anti-pathogenic agents. Thus, the genes can be used to engineer plants having disease resistance or increased disease resistance. Likewise, the sequences find use in engineering plants for enhanced response to stress including pathogen attack, wounding, and abiotic stress. Such abiotic stress includes heat, drought, cold, reactive oxygen species, radiation, and the like. In this manner, the sequences can be used alone or in combination with each other and/or with other known disease resistance genes to provide broad-spectrum disease resistance.

Additionally, the sequences can be used as markers in studying defense signal pathways and in disease-resistance breeding programs. The sequences can also be used as probes to isolate other signaling components involved in defense/resistance responsiveness and to isolate the corresponding promoter sequences. See, generally, Sambrook et al. (1989) *Molecular Cloning: A Laboratory Manual* (2d ed., Cold Spring Harbor Laboratory Press, Plainview, N.Y.).

Compositions of the invention include the nucleotide sequences for a maize gene designated herein as the major latex gene set forth in SEQ ID NO:1, and the corresponding amino acid sequence for the protein encoded thereby (set forth in SEQ ID NO:2). Fragments and variants of these sequences as defined herein are also encompassed by the present invention. These gene sequences may be assembled into a DNA construct such that the gene is operably linked to a promoter that drives expression of a coding sequence in a cell of interest. Plants stably transformed with this DNA construct express a protein of the invention. Expression of this protein creates or enhances disease resistance in the transformed plant.

Fragments and variants of the major latex sequences disclosed herein are encompassed by the present invention. A fragment of a nucleotide sequence may encode a biologically active portion of a major latex protein, or it may be a fragment that can be used as a hybridization probe or PCR primer using methods described below. A biologically active portion of a major latex polypeptide can be prepared by isolating a portion of one of the maize major latex nucleotide sequence of the invention, expressing the encoded portion of the major latex protein (e.g., by recombinant expression in vitro), and assessing the anti-pathogenic activity of the encoded portion of the polypeptide. Nucleic acid molecules that are fragments of a maize major latex nucleotide sequence comprise at least 16, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, or 825 nucleotides, or up to the number of nucleotides present in a full-length maize major latex nucleotide sequence disclosed herein (for example, 835 nucleotides for SEQ ID NO:1).

It is recognized that with these nucleotide sequences, antisense constructions complementary to at least a portion of the mRNA for the anti-pathogenic sequences can be constructed. Antisense nucleotides are constructed to hybridize with the corresponding mRNA. Modifications of the antisense sequences may be made as long as the sequences hybridize to and interfere with expression of the corresponding mRNA. Antisense constructions having 70%, preferably 80%, more preferably 85%, 90%, 95% up to 100% sequence identity to the corresponding antisense sequences may be used. Furthermore, portions of the antisense nucleotides may be used to disrupt the expression of the targeted gene. Thus, production of the native protein encoded by the targeted gene can be inhibited to achieve a desired phenotypic response. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323, herein incorporated by reference.

A fragment of the maize major latex nucleotide sequence that encodes a biologically active portion of the major latex protein of the invention will encode at least 15, 25, 30, 50, 75, 100, 110, 120, 130, or 140 contiguous amino acids, or up to the total number of amino acids present in a full-length protein of the invention (for example 154 amino acid residues for SEQ ID NO:2). Fragments of a maize major latex nucleotide sequence that are useful as hybridization probes or PCR primers generally need not encode a biologically active portion of a major latex protein.

In this manner, the present invention encompasses the anti-pathogenic proteins as well as fragments thereof. That is, it is recognized that fragments of the proteins may be produced which retain anti-pathogenic protein activity that creates or enhances disease resistance in a plant. These fragments include truncated sequences, as well as N-terminal, C-terminal, internal, and internally deleted amino acid sequences of the proteins.

The proteins of the invention may be altered in various ways including amino acid substitutions, deletions, truncations, and insertions to obtain variant proteins that continue to possess the desired anti-pathogenic activity of the native proteins disclosed herein. Methods for such manipulations are generally known in the art. For example, amino acid sequence variants of the proteins can be prepared by mutations in the DNA. Methods for mutagenesis and nucleotide sequence alterations are well known in the art. See, for example, Kunkel (1985) *Proc. Natl. Acad. Sci. USA*

82:488–492; Kunkel et al. (1987) *Methods in Enzymol.* 154:367–382; U.S. Pat. No. 4,873,192; Walker and Gaastra, eds. *Techniques in Molecular Biology* (MacMillan Publishing Company, New York) and the references cited therein. Guidance as to appropriate amino acid substitutions that do not affect desired biological activity of the native protein may be found in the model of Dayhoff et al. (1978) *Atlas of Protein Sequence and Structure* (Nat'l Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass the naturally occurring proteins as well as variations and modified forms thereof. Obviously, the mutations that will be made in the DNA encoding the variant must not place the sequence out of reading frame and preferably will not create complementary regions that could produce secondary mRNA structure. See generally EP Patent Application Publication No. 75,444.

The deletions, insertions, and substitutions of the protein sequences encompassed herein are not expected to produce radical changes in the characteristics of the anti-pathogenic proteins. However, when it is difficult to predict the exact effect of the substitution, deletion, or insertion in advance of doing so, one skilled in the art will appreciate that the effect will be evaluated by routine screening assays. That is, the activity of the modified protein sequences can be evaluated by monitoring of the plant defense system. See, for example U.S. Pat. No. 5,614,395, herein incorporated by reference.

Variant nucleotide sequences and proteins also encompass anti-pathogenic genes and proteins derived from a mutagenic and recombinogenic procedure such as DNA shuffling. With such a procedure, one or more different anti-pathogenic gene or protein sequences can be manipulated to create new sequences possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the maize major latex gene of the invention and other known anti-pathogenic genes to obtain a new gene encoding a protein with an improved property of interest, such as a broader spectrum of pathogen resistance. Likewise, sequences corresponding to regulatory motifs, such as specific cis-acting elements within the promoters of the invention may be shuffled creating improved regulatory functions, such as increased pathogen inducibility. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire anti-pathogenic promoters and genes of the present invention or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have promoter activity or encode for a plant major latex protein and which hybridize under stringent conditions to the sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the maize major latex sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire anti-pathogenic coding sequence or portion thereof, may be used as a probe capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the anti-pathogenic coding sequences from a chosen organism by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions as qualified elsewhere herein. Isolated sequences that have anti-pathogenic activity and which hybridize under stringent conditions to the major latex gene sequence disclosed herein, or to fragments thereof, are encompassed by the present invention.

While the invention is not bound by any particular mechanism of action, the gene products, probably proteins or polypeptides, function to inhibit or prevent plant diseases in a plant. Such gene products may be anti-pathogenic. That is, such gene products may be capable of suppressing, controlling, and/or killing the invading pathogenic organism. It is recognized that the present invention is not dependent upon a particular mechanism of defense. Rather, the genes and methods of the invention work to increase resistance of the plant to pathogens independent of how that resistance is brought about.

The anti-pathogenic genes and proteins of the invention, as well as fragments and variants thereof, can also be used to control resistance to pathogens by creating or enhancing defense mechanisms in a plant. While the exact function of the anti-pathogenic proteins is not known, these proteins are involved in influencing the expression of defense-related proteins. It is recognized that the present invention is not premised upon any particular mechanism of action of the anti-pathogenic genes. It is sufficient for purposes of the invention that the genes and proteins are involved in the plant defense system and can be used to create or increase resistance levels in the plant to pathogens.

The plant defense mechanisms described herein may be used alone or in combination with other proteins or agents to protect against plant diseases and pathogens. Other plant defense proteins include those described in the copending application entitled "Methods for Enhancing Disease Resistance in Plants," U.S. application Ser. No. 09/256,898, filed Feb. 24, 1999, the copending application entitled "Genes for Activation of Plant Pathogen Defense Systems," U.S. application Ser. No. 09/256,158, filed Feb. 24, 1999, and WO 99/43819, published Sep. 9, 1999, all of which are herein incorporated by reference.

The anti-pathogenic nucleotide sequences of the invention are provided in expression cassettes for expression in the plant of interest as described below. The cassette will include 5' and 3' regulatory sequences operably linked to an anti-pathogenic sequence of the invention.

A number of promoters can be used to drive the expression of the coding sequences encoding the anti-pathogenic proteins of the invention. The promoters may be selected based on the desired outcome. For example, the promoters may be selected based on desired timing, localization, and/or level of expression of the anti-pathogenic genes in a plant. Constitutive, tissue-preferred, pathogen-inducible, and wound-inducible promoters can be used in the practice of the invention. The promoter used to regulate expression of the claimed nucleotide sequence may be homologous to the claimed nucleotide sequence. In these cases, the transformed plant will have a change in phenotype. The anti-pathogenic coding sequences of the invention may be expressed by promoters that are native or analogous or foreign or heterologous to the operably linked coding sequence. A number of heterologous promoters can be used toward this end.

It may be beneficial to express the gene from an inducible promoter, particularly a pathogen-inducible promoter. The inducible promoter will initiate expression of a gene in the presence of a pathogen to prevent infection and disease symptoms. Such promoters include those from other pathogenesis-related proteins (PR proteins), which are induced following infection by a pathogen; e.g., PR proteins, SAR proteins, beta-1, 3-glucanase, chitinase, etc. See, for example, Redolfi et al. (1983) *Neth. J. Plant Pathol.* 89:245–254; Uknes et al. (1992) *Plant Cell* 4:645–656; Van Loon (1985) *Plant Mol. Virol.* 4:111–116; see also WO 99/43819, published Sep. 9, 1999, herein incorporated by reference.

Of interest are promoters that are expressed locally at or near the site of pathogen infection. See, for example, Marineau et al. (1987) *Plant Mol. Biol.* 1:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan et al. *Ann. Rev. Phytopath.* 28:425–449; Duan et al. *Nature Biotechnology* 14:494–498); wun1 and wun2, U.S. Pat. No. 5,428,148; win1 and win2 (Stanford et al. *Mol. Gen. Genet.* 215:200–208); systemin (McGurl et al. *Science* 225:1570–1573); WIP1 (Rohmeier et al. *Plant Mol. Biol.* 22:783–792; Eckelkamp et al. *FEBS Letters* 323:73–76); MPI gene (Corderok et al. *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142.

Tissue-preferred promoters can be used to target antipathogenic gene expression within a particular tissue. Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2): 207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759–772); and rolB promoter (Capana et al. (1994) *Plant Mol. Biol.* 25(4):681–691. See also U.S. Pat. Nos. 5,837,876; 5,750,386; 5,633,363; 5,459,252; 5,401,836; 5,110,732; and 5,023,179.

Promoters

The invention also encompasses the 5' regulatory regions of the maize major latex gene disclosed herein. The nucleotide sequences for the native 5' untranslated regions, i.e., promoters, are provided in SEQ ID NO:3. It is recognized that, having identified the nucleotide sequences for the promoter regions disclosed herein, it is within the state of the art to isolate and identify further regulatory elements in the 5' untranslated region and in the untranslated region located upstream from the particular promoter regions identified herein. Thus, for example, the promoter regions disclosed herein may further comprise upstream regulatory elements that confer tissue-specific and/or tissue-preferred expression of any heterologous nucleotide sequence operably linked to one of the disclosed promoter sequences. See particularly Australian Patent No. AU-A-77751/94 and U.S. Pat. Nos. 5,466,785 and 5,635,618. Likewise, promoter regions having homology to the promoters of the invention can be isolated by hybridization under stringent conditions, as described elsewhere herein.

Such regulatory elements may or may not be similar to previously reported elements from other genes, regulatory regions, and/or organisms. For example, the maize major latex promoter disclosed herein comprises a TATA box at nucleotide position 1013 to 1022, namely "TATATATA." This sequence may assume a Z-DNA configuration. Z-DNA may play a role in gene transcriptional regulation. G-boxes (GACGTG) and the closely related ACGT boxes are often found in plant gene promoters. In the Zm-MLP-1 gene there is no perfect match to "CACGTG," but there is a single ACGT box at position 963–966. The ACGT box in the Zm-MLP1 gene contains the following sequence context "GC<u>ACGTCA</u>" at positions 961–968, which shares a high degree of identity to a wheat histone gene promoter (Ohtsubo et al. (1997) *Plant J.* 11:1219–1225) and a rice histone gene ACGTCA (Terada et al. (1995) *Plant Mol. Biol.* 27:17–26). ACGR boxes may be responsible for binding the bZIP transcription factors, which appear to regulate the expression of many genes (Feldgrugge et al. (1996) *Mol. Gen. Genet.* 6:619–627). There is a potential CAAT box at position 887–890 in the sequence "CGCAATTG."

Other elements that may be present in the promoter sequence of the invention include 35S core enhancer-like elements, such as "GTGGATTA" (at nucleotide (nt) 183–190), "CAATCCAC" (at nt 340–347), and "GTG-GTTG" (at nt 911–917). Also, other elements that may be present include an "L-box element similar to that in the parsley caffeoyl-CoA-methyl transferase gene that is thought to be involved in induction in response to stress. The Zm-MLP1 5' region contains "TCTCACCATCG" at position 1038–1048 and matches the "L" box at 9/11 positions.

Palindromic sequences are features of plant gene promoters that are sometimes implicated in transcriptional control. For example, the Ocs gene contains a 16 bp palindromic sequence (Ellis et al. (1987) *EMBO J* 6:3203–3208). The Zm-MLP1 gene contains several novel palindromic sequences including the 10 base palindrome "GACGGC-CGTC" at position 147–156, and the 10 base palindrome "GCAGTACTGC" at position 619–628; and the 14 base palindrome "GTTCCGGCCGGAAC" at position 666–679, and the 11 base palindrome "AATTGAATT" at position 888–896.

GCC boxes are implicated in defense, stress, ABA, and ethylene mediated regulation in plant genes. A closely related sequence "GCCCGGC" was identified (at nt 942–946) which is likely to have GCC box activity (Kitajima et al (1998) *Plant Cell Reports* 18:173–179; and Sessa et al. (1995) *Plant Mol. Biol.* 28:145–153).

It is recognized in the art that regulatory elements can interact to produce a variety of regulation patterns. Such regulation may vary depending on the identity, location, and relative spacing of such elements and the coding sequence regulated thereby. Thus, regulatory elements in the disclosed promoter sequence may additionally provide compositions for and methods with which one of skill can design a desired synthetic promoter or set of regulatory elements to control gene expression in a desirable manner. One of skill can assay the function of potentially useful regulatory elements using expression assays known in the art. For example, a candidate regulatory element may be assayed by operably linking the regulatory element to an appropriate marker gene so that expression of the marker gene is under control of the candidate regulatory element, transforming this assembly into plants, and monitoring expression of the marker gene for desired patterns of expression, with or without the addition of various stimuli.

The promoter sequences of the invention include both the naturally occurring sequences as well as mutant forms. Additionally, sequences corresponding to regulatory motifs, such as specific cis-acting elements within the promoters of the invention, may be shuffled, creating improved regulatory functions, such as increased pathogen inducibility. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotechnology* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

Fragments and variants of the promoter nucleotide sequences disclosed herein are also encompassed by the present invention. A fragment of a maize major latex promoter nucleotide sequence comprises at least 15, 20, 25, 30, 35, 40, 45, 50, 75, 100, 325, 350, 375, 400, 425, 450, 500, 550, 600, 650, 700, 750, 800, 850, 900, 950, or 1000 nucleotides, or up to the number of nucleotides present in a full-length promoter nucleotide sequence disclosed herein (for example, 1030 nucleotides for SEQ ID NO:3). Generally, fragments of a promoter sequence that retain their biological activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are encompassed by the compositions of the present invention.

The nucleotide sequences for the inducible promoters disclosed in the present invention, as well as variants and fragments thereof, are useful in the genetic manipulation of any plant when assembled within a DNA construct such that the promoter sequence is operably linked with a heterologous nucleotide sequence whose inducible expression is to be controlled to achieve a desired phenotypic response. It is recognized that the promoter sequences of the invention may also be used with their native coding sequences to increase or decrease expression of the native coding sequence, thereby resulting in a change in phenotype in the transformed plant.

The promoters of the invention can be used to regulate expression of any nucleotide sequence of interest in order to vary the phenotype of a plant. Such expression may be regulated by the promoters of the invention in an inducible manner. Various changes in phenotype are of interest. Nucleotide sequences of interest include, for example, disease resistance genes, insect resistance genes, and the like. Other sequences of interest include antisense nucleotide sequences.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; and U.S. Pat. Nos. 5,703,049, 5,885,801, and 5,885,802, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; Geiser et al. (1986) *Gene* 48:109); lectins (Van Damme et al. (1994) *Plant Mol Biol.* 24:825); protease inhibitors (Ryan et al. (1990) *Ann. Rev. Phytopathol,* 28:425–449); tachyplesin (U.S. patent application Ser. No. 08/962,034); amylase inhibitors (Fung et al. (1996) *Insect Biochem. Mol. Biol.* 26(5):419–426, and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; Mindrinos et al. (1994) *Cell* 78:1089); and the like.

Expression Cassettes

In some embodiments, isolated nucleic acids which serve as a promoter or enhancer elements can be introduced in the appropriate position (generally upstream) of a non-heterologous form of a polynucleotide of the present invention so as to up or down modulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

The nucleotide sequences of the invention are provided in expression cassettes for use in the plant of interest. Expression cassettes may comprise any of the nucleotide sequences of the invention For example, expression cassettes or DNA constructs of the invention may be provided with a plurality of restriction sites for insertion of the anti-pathogenic sequence to be under the transcriptional regulation of the regulatory regions. Expression cassettes or DNA constructs may also be provided with a plurality of restriction sites for insertion of a sequence of interest to be placed under the regulatory influence of the promoters of the invention. The expression cassettes may additionally contain at least one additional gene to be cotransformed into the organism. Alternatively, the additional gene(s) can be provided on multiple expression cassettes. The expression cassette may additionally contain selectable marker genes.

The expression cassettes or DNA constructs of the invention will include in the 5'-to-3' direction of transcription, a transcriptional and translational initiation region, a nucleotide sequence to be expressed, and a transcriptional and translational termination region functional in plants. The transcriptional initiation region, the promoter, may be native or analogous or foreign or heterologous to the plant host. The promoter may also be native or analogous or foreign or heterologous to the nucleotide sequence or coding sequence to be expressed. Additionally, the promoter may be the natural sequence or alternatively a synthetic sequence.

While it may be preferable to express the sequences encoding the anti-pathogenic proteins using heterologous promoters, the native promoter sequences may be used. Such constructs would change expression levels of the anti-pathogenic genes in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acids Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology, Vol. 78* (Springer-Verlag, Berlin); Gill et al. (1988) *Nature* 334:721–724; etc. Such disclosures are herein incorporated by reference. The above list of selectable marker genes is not meant to be limiting. Any selectable marker gene can be used in the present invention.

It is further recognized that the components of the expression cassettes may be modified to increase expression. For example, truncated sequences, nucleotide substitutions, or other modifications may be employed. See, for example Perlak et al. (1991) *Proc. Natl. Acad. Sci. USA* 88:3324–3328; Murray et al. (1989) *Nucleic Acids Res.* 17:477–498; and WO 91/16432.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94; untranslated leader from the coat protein mRNA of alfalfa mosaic virus (AMV RNA 4) (Jobling et al. (1987) *Nature* 325:622–625); tobacco mosaic virus leader (TMV) (Gallie. (1989) *Molecular Biology of RNA*, ed. Cech (Liss, N.Y.) pp. 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

Transformation

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Pnaicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (Coffea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g. *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

Pathogens and Pests

The invention is drawn to compositions and methods for inducing resistance in a plant to plant pests. Accordingly, the compositions and methods are also useful in protecting plants against fingal pathogens, viruses, nematodes, insects, and the like.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, aclear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267:2228–2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotiun rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campes-* tris p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*; Alfalfa: *Clavibater michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, Fusarium, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Plasmophora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillusflavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *Colletotrichum graminicola* (*Glomerella graminicola*), *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Perconia circinata*, *Fusarium moniliforme*, *Alternaria alternata*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari*, *Sporisorium reilianum* (*Sphacelotheca reiliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*, etc.

Nematodes include parasitic nematodes such as root-knot, cyst, and lesion nematodes, including Heterodera and Globodera spp; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

Molecular Markers

The present invention provides a method of genotyping a plant comprising a polynucleotide of the present invention. The plant may be a monocot, such as maize or sorghum, or alternatively, a dicot, such as sunflower or soybean. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, ed. (1997) *Plant Molecular Biology: A Laboratory Manual*, Chapter 7 (Springer-Verlag, Berlin). For molecular marker methods, see generally, Paterson (1996) "The DNA Revolution," in *Genome Mapping in Plants*, ed. Paterson (Academic Press/ R. G. Landis Company, Austin, Tex.), pp. 7–21.

The particular method of genotyping in the present invention may employ any number of molecular marker analytic techniques such as, but not limited to, restriction fragment length polymorphisms (RFLPs). Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the invention.

In the present invention, the nucleic acid probes employed for molecular marker mapping of plant nuclear genomes selectively hybridize, under selective hybridization conditions, to a gene encoding a polynucleotide of the present invention. In some embodiments, the probes are selected from polynucleotides of the present invention. Typically, these probes are cDNA probes or Pst I genomic clones. The length of the probes is discussed in greater detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In some embodiments, the nucleic acid probe comprises a polynucleotide of the present invention.

RNA Profiling

RNA profiling (or "gene expression profiling") is typically used to compare gene expression between two distinct biological states of any organism such as, for example, a comparison of an uninfected plant and an infected plant. Using this method, specific genes may be identified that display differences in expression between the two biological states. For example, differences in the expression of specific genes between uninfected and pathogen-challenged maize plants can be determined using gene expression profiling. Probes derived from the Zm-MLP1 nucleotide sequence of the present invention can be used in this way to determine differences in gene expression in pathogen-challenged or infected plants. mRNA can be analyzed using the gene expression profiling process (GeneCalling®) as described in U.S. Pat. No. 5,871,697, herein incorporated by reference.

Formulations

Methods are provided for controlling plant pathogens comprising applying an anti-pathogenic amount of a polypeptide or composition of the invention to the environment of the pathogens. The polypeptides of the invention can be formulated with an acceptable carrier into a pesticidal composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb–5.0 lb per acre when in dry form and at about 0.01 pts-10 pts per acre when in liquid form.

In a further embodiment, the compositions, as well as the proteins of the present invention can be treated prior to formulation to prolong the activity when applied to the environment of a target pest as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.).

The compositions can be applied to the environment of a pest by, for example, spraying, atomizing, dusting, scattering, coating or pouring, introducing into or on the soil, introducing into irrigation water, by seed treatment, or dusting at the time when the pest has begun to appear or before the appearance of pests as a protective measure. It is generally important to obtain good control of pests in the early stages of plant growth, as this is the time when the plant can be most severely damaged. The compositions of the invention can conveniently contain another insecticide or pesticide if this is thought necessary.

In a further embodiment, formulations of the present invention for use as antimicrobial therapies comprise the anti-pathogenic proteins in a physiologically or pharmaceutically acceptable carrier, such as an aqueous carrier. Thus, formulations for use in the present invention include, but are not limited to, those suitable for parenteral administration, including subcutaneous, intradermal, intramuscular, intravenous and intraarterial administration, as well as topical administration. The formulations may conveniently be presented in unit dosage form and may be prepared by any of the methods well known in the art. Such formulations are described in, for example, *Remington's Pharmaceutical Sciences* (19th ed., Mack Pub. Co., Easton, Pa., 1995).

In the manufacture of a medicament according to the invention, the anti-pathogenic compositions are typically admixed with, inter alia, an acceptable carrier. The carrier must, of course, be acceptable in the sense of being compatible with any other ingredients in the formulation and must not be deleterious or harmful to the patient. The carrier may be a solid or a liquid. One or more anti-pathogenic proteins may be incorporated in the formulations of the invention, which may be prepared by any of the well-known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants, buffers, bacteriostats, and solutes that render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation, the anti-pathogenic protein may be contained within a lipid particle or vesicle, such as a liposome or microcrystal, which may be suitable for parenteral administration. The particles may be of any suitable structure, such as unilamellar or plurilamellar, so long as the targeted cassette is contained therein. Positively charged lipids such as N-[1-(2,3-dioleoyloxi)propyl]-N,N, N-trimethyl-amoniummethylsulfate, or "DOTAP", are particularly preferred for such particles and vesicles. The preparation of such lipid particles is well known. See, e.g., U.S. Pat. Nos. 4,880,635; 4,906,477; 4,911,928; 4,917,951; 4,920,016; 4,921,757; etc.

The dosage of the anti-pathogenic polypeptide administered will vary with the particular method of administration, the condition of the subject, the weight, age, and sex of the subject, the particular formulation, the route of administration, etc. In general, the protein will be administered in a range of about 1 $\mu$g/L to about 10 g/L.

In an embodiment of the invention, the anti-pathogenic polypeptides of the invention can be used for any application including coating surfaces to target microbes. In this manner, the target microbes include human pathogens or microorganisms. Surfaces that might be coated with the anti-pathogenic polypeptides of the invention include carpets and sterile medical facilities. Polymer bound polypeptides of the invention may be used to coat surfaces. Methods for incorporating compositions with anti-microbial properties into polymers are known in the art. See U.S. Pat. No. 5,847,047 herein incorporated by reference.

This invention can be better understood by reference to the following non-limiting examples. It will be appreciated by those skilled in the art that other embodiments of the invention may be practiced without departing from the spirit and scope of the invention as herein discussed.

Experimental

EXAMPLE 1

Transformation and Regeneration of Transgenic Plants

Immature maize embryos from greenhouse donor plants are bombarded with a plasmid containing the Zm-MLP1 gene operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the Zm-MLP1 coding sequence operably linked to a ubiquitin promoter is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water

10 $\mu$l (1 $\mu$g) DNA in Tris EDTA buffer (1 $\mu$g total DNA)

100 $\mu$l 2.5 M $CaCl_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry for about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the nucleotide.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 2

Azrobacterium-mediated Transformation of Maize

For Agrobacterium-mediated transformation of maize with a Zm-MLP1 nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the nucleotide sequence of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 3

Soybean Embryo Transformation

Soybean embryos are bombarded with a plasmid containing a Zm-MLP1 nucleic acid operably linked to an ubiquitin promoter as follows. To induce somatic embryos, cotyledons 3–5 mm in length are dissected from surface-sterilized, immature seeds of the soybean cultivar A2872 and cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml of liquid media on a rotary shaker at 150 rpm and 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al., Nature 327:70–73 (1987)); U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al., Nature 313:810–812 (1985)), the hygromycin phosphotransferase gene from plasmid pJR225 (from E. coli; Gritz et al., Gene 25:179–188 (1983)), and the 3' region of the nopaline synthase gene from the T-DNA of the Agrobacterium tumefaciens Ti plasmid. The expression cassette comprising the Zm-MLP1 sequence operably linked to the promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µl/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/ particle suspension can be sonicated three times for one second each. Five microliters of the DNA-coated gold particles are then loaded on each macrocarrier disk.

Approximately 300–400 mg of a two-week-old suspension culture is placed in an empty 60×15 mm Petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 4
Detection of Expression of Maize Major Latex Protein Gene

For transformation experiments to produce transgenic ERE-avrRxv callus, immature embryos were isolated from greenhouse-grown HiII genotype maize plants 8–10 days after pollination. The immature embryos were isolated, cultured and prepared for bombardment as described above for the transient expression assays. Particle bombardment transformation was done as described elsewhere herein for immature embryo transformation, except that the transforming DNA was PHP12242, the "ERE-avrRxv" construct. This construct places the transcription of an avrRxv nucleotide sequence under control of the estrogen receptor; thus, expression of avrRxv can be induced with estradiol and/or estradiol analogs in transgenic plants containing this construct.

One day after 745 embryos were bombarded, they were transferred to a selection medium similar to the initiation medium but containing 3 mg/L active ingredient of the herbicide bialaphos® (Meiji Seika Kaisha, LTD, Yokohama, Japan). From these, 48 transformed colonies were identified between 7 and 9 weeks after bombardment and selected by rapid, healthy growth. Of these 33 were PCR positive for the avrRxv gene, among them lines 197 and 186 described herein. Cell suspensions were generated from ERE-avrRxv callus line 197 and control HiII callus by forcing calli through a 1.5 mm sieve into 250 ml baffled flasks containing 70 ml of liquid Murashige and Skoog (MS) medium with MS vitamins, 3% sucrose, 2 mg/L 2,4-D. Flasks were rotated at 140 rpm in the dark at 28° C., and transfers were performed twice weekly, with periodic selections for smaller cell aggregates, with transferred cells kept to approximately 5 ml of packed volume.

Transformed callus and cell suspensions were treated with estradiol to induce avrRxv gene expression. For callus treatment, the callus tissue was gently broken up into 10–20 mg pieces and then plated on the N6 agar medium described above. Three callus lines were used: HiII::nontransformed control, HiII::ERE-avrRxv line 197 and HiII::ERE-avrRxv line 186. For the experimentals ethanyl-estradiol (Sigma, St. Louis, Mo.) was dissolved in 100% ethanol to a 10 mM concentration, and then 34.8 μl of this stock was dispersed in 4 ml of $H_2O$ for an 87 μM final concentration. For the controls 34.8 μl of 100% ethanol was added to 4 ml of water. The 4 ml of solution was spread over the agar surface of 100×25 mm plates, flooding the callus cells. The plates were dried in a sterile flow hood overnight, then covered and further incubated at 23° C. in the dark, with reapplication after 72 hours. For cell suspension cultures about 5 ml of cells in a 70 ml of liquid culture received either 70 μl of 10 mM estradiol in 100% ethanol (final concentration 10 μM estradiol and 0.1% ethanol) or ethanol only for controls. At the desired timepoints, cells were collected by centrifugation.

EXAMPLE 5 mRNA Abundance Profiling

Protocols for preparing in vitro-transcribed biotinylated cRNA probes from poly-$A^+$ mRNA for Affymetrix GeneChip® gene expression analysis were according to the manufacturer's recommendations (Affymetrix, Santa Clara, Calif.), which are described in Wodicka et al, 1997. In brief, per sample 2 μg of poly-$A^+$ mRNA, described above in mRNA isolations, was used for the first strand cDNA synthesis. This involved a T7-$(dT)_{24}$ oligonucleotide primer and reverse transcriptase SuperScript II (Gibco-BRL, Gaithersburg, Md.). The second strand synthesis utilized *E. coli* DNA Polyimerase I (Gibco-BRL, Gaithersburg, Md.). The double-stranded cDNA was then purified using phenol/chloroform extraction and phase lock gels (5 Prime-3 Prime, Inc., Boulder, Colo.) followed by ethanol precipitation. For the in vitro transcription to produce cRNA, biotin-11-CTP and biotin-16-UTP, in addition to all four NTPs, were used with T7 transcriptase (Ambion, Austin, Tex.). The IVT product was purified using Rneasy affinity resin columns (Qiagen, Chatsworth, Calif.). Labeled in vitro transcript (IVT) yields ranged from 62–80 μg per sample. They were stored at −80° C. until use. The IVT products were fragmented in acetate buffer (pH 8.1) at 94° C. for 35 minutes prior to chip hybridization.

The 1.28 cm×1.28 cm GeneChip® contain a high-density array of 20-mer oligonucleotides affixed to a silicon wafer. These oligonucleotides were synthesized in situ on the silicon wafer by a light-dependent combinatorial chemical synthesis (Fodor et al., 1991; Pease et al., 1994). The oligonucleotide sequences are complementary to the sense strand of cDNA EST sequences. For each gene there are up to forty 20-mer oligonucleotides synthesized. Twenty of these oligonucleotides are exact matches to different, though sometimes overlapping, regions of the EST sequence. The other 20 oligonucleotides contain one base mismatch in the center, which changes hybridization efficiency. (For a minority of genes there were less than 20 oligo probe pairs, but never less than 15 pairs per gene). The perfect match (PM) and mismatch (MM) oligo probe pairs for each gene are tiled in adjacent regions of the GeneChip. Comparison of the hybridization intensities between different PM oligonucleotides for a given gene, and between PM to MM hybridization intensities for an oligonucleotide pair, are used to determine the overall hybridization to the gene, and hence its level of mRNA abundance in the samples (see Wodicka et al., 1997).

Probes of in vitro labeled transcript were prepared for each of the following four samples obtained as described in Example 4: 1) HiII callus control (not estradiol treated); 2) HiII callus, estradiol treated; 3) ERE-avrRxv callus (line 197) control; and 4) ERE-avrRxv callus (line 197) estradiol treated. Twelve μg IVT for each sample were used per chip hybridization. Each sample was hybridized twice (reps A and B), each rep using a different chip. Hybridization and image scanning conditions, and quantitative analysis and intensity calculations, were essentially as described (Wodicka et al., 1997). Comparisons of mRNA levels were made between each rep of each sample, for a total of 8 comparisons. Positive gene expression changes were defined as those showing a 2-fold or more change in at least three of these four comparisons made between the HiII control and ERE-avrRxv genotypes.

Initial data from this experiment indicated that the Zm-MLP1 gene is up-regulated by induction of avr gene expression in this transgenic line. Northern blot assay data (shown in FIG. 1) confirmed that avrRxv expression induced expression of the Zm-MLP1 gene. Because this avrRxv-induced expression is first detected about an hour after estradiol treatment, induction of the Zm-MLP1 gene is induced very shortly after avrRxv induction. Therefore, this gene and its promoter have significant potential utility for engineering a rapidly-inducible disease- or stress-resistance in crop plants. In one embodiment, the promoter could also be used to drive the expression of other and/or additional gene products that could contribute to disease resistance, such as, for example, antimicrobial proteins, chitinases, R genes, and the like.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule having a nucleotide sequence for a promoter that is capable of initiating transcription in a plant cell, wherein said nucleotide sequence for said promoter is selected from the group consisting of:
   a. a nucleotide sequence comprising the sequence set forth in NO:3;
   b. a nucleotide sequence comprising at least 30 contiguous nucleotide of the sequence set forth in SEQ ID NO:3; and
   c. a nucleotide sequence that hybridizes under stringent conditions to a sequence of a) or b).

2. A DNA construct comprising a nucleotide sequence of claim 1 operably linked to a heterologous nucleotide sequence of interest.

3. A vector comprising the DNA construct of claim 2.

4. A host cell having stably incorporated in its genome the DNA construct of claim 2.

5. A method for inducing expression of a heterologous nucleotide sequence in a plant, said method comprising transforming a plant cell with a DNA construct comprising said heterologous nucleotide sequence operably linked to a promoter that is capable of initiating transcription in a plant cell in response to a stimulus, regenerating a stably transformed plant from said plant cell, and exposing said plant to said stimulus, wherein said promoter comprises a nucleotide sequence selected from the group consisting of:
   a. a nucleotide sequence comprising the sequence set forth in SEQ NO:3;
   b. a nucleotide sequence comprising at least 30 contiguous nucleotides of the sequence set forth in SEQ ID NO:3; and
   c. a nucleotide sequence that hybridizes under stringent conditions to a sequence of a) or b).

6. The method of claim 5, wherein said plant is a monocot.

7. The method of claim 6, wherein said monocot is maize.

8. The method of claim 5, wherein said plant is a dicot.

9. A plant cell stably transformed with a DNA construct comprising a heterologous nucleotide sequence operably linked to a promoter that is capable of initiating transcription in said plant cell, wherein said promoter comprises a nucleotide sequence selected from the group consisting of:
   a. a nucleotide sequence comprising the sequence set forth in SEQ ID NO:3;
   b. a nucleotide sequence comprising at least 30 contiguous nucleotides of the sequence set forth in SEQ ID NO:3; and
   c. a nucleotide sequence that hybridizes under stringent conditions to a sequence of a) or b).

10. The plant cell of claim 9, wherein said plant cell is from a monocot.

11. The plant cell of claim 10, wherein said monocot is maize.

12. The plant of claim 9, wherein said plant cell is from a dicot.

13. A plant stably transformed with a DNA construct comprising a heterologous nucleotide sequence operably linked to a promoter that is capable of initiating transcription in a plant cell, wherein said promoter comprises a nucleotide sequence selected from the group consisting of:
   a. a nucleotide sequence comprising the sequence set forth in SEQ ID NO:3;
   b. a nucleotide sequence comprising at least 30 contiguous nucleotides of the sequence set forth in SEQ ID NO:3; and
   c. a nucleotide sequence that hybridizes under stringent conditions to a sequence of a) or b).

14. The plant of claim 13, wherein said plant is a monocot.

15. The plant of claim 14, wherein said monocot is maize.

16. The plant of claim 13, wherein said plant is a dicot.

17. Transformed seed of the plant of claims 13.

* * * * *

UNITED STATES PATENT AND TRADEMARK OFFICE
CERTIFICATE OF CORRECTION

PATENT NO. : 6,861,577 B2
DATED : March 1, 2005
INVENTOR(S) : Pedro A. Navarro Acevedo et al.

Page 1 of 1

It is certified that error appears in the above-identified patent and that said Letters Patent is hereby corrected as shown below:

Title page,
Item [57], ABSTRACT, should read:
-- The invention is drawn to the promoter of a major latex protein gene from maize, which is pathogen-activated. The promoter can be used in methods of expressing a heterologous DNA sequence in plants. --

Column 43,
Line 12, should read -- 1. An isolated nucleic acid molecule comprising SEQ ID NO: 3. --
Line 23, should read -- 2. A DNA construct comprising the nucleotide sequence of --
Line 29, should read -- 5. A method for expressing a heterologous nucleotide sequence in a plant, wherein said method comprises transforming a plant cell with the DNA construct of claim 2, and regenerating a stably transformed plant from said plant cell. --

Column 44,
Line 11, should read -- 9. A plant cell stably transformed with the DNA construct of claim 2. --
Line 28, should read -- 12. The plant cell of claim 9, wherein said plant cell is from --
Line 30, should read -- 13. A plant stably transformed with the DNA construct of claim 2. --
Line 46, should read -- 17. Transformed seed of the plant of any one of claims 13-16, wherein the seed comprises the DNA construct. --

Signed and Sealed this

Fifth Day of July, 2005

JON W. DUDAS
*Director of the United States Patent and Trademark Office*

SEQUENCE LISTING

<160> NUMBER OF SEQ ID NOS: 3

<210> SEQ ID NO 1
<211> LENGTH: 835
<212> TYPE: DNA
<213> ORGANISM: Zea mays
<220> FEATURE:
<221> NAME/KEY: CDS
<222> LOCATION: (78)...(542)

<400> SEQUENCE: 1

```
ggcgaggtct caccatcgcc agacacacta tagaccacag ccagtcagcc acatcactag        60
ctatctgtgc agaggca atg gcg tcc aag gtt gag ctg gtg gtg gag gtc          110
                Met Ala Ser Lys Val Glu Leu Val Val Glu Val
                 1               5                  10 aag tcc ccg gct gac aag ctg tgg gcg gcg ctg cgt gac tcg acg gag         158
Lys Ser Pro Ala Asp Lys Leu Trp Ala Ala Leu Arg Asp Ser Thr Glu
             15                  20                  25 ctg ttc ccc aag atc ttc ccc gag cag tac aag agc atc gag acc gtc         206
Leu Phe Pro Lys Ile Phe Pro Glu Gln Tyr Lys Ser Ile Glu Thr Val
         30                  35                  40 gag ggc gac ggc aag tcg gcc ggc acc gtc cgc ctc ctc aag tac acc         254
Glu Gly Asp Gly Lys Ser Ala Gly Thr Val Arg Leu Leu Lys Tyr Thr
     45                  50                  55 gag gcg gtg ccg atg ctg acg ttc gcc aag gag aag ctt gag acg gcg         302
Glu Ala Val Pro Met Leu Thr Phe Ala Lys Glu Lys Leu Glu Thr Ala
 60                  65                  70                  75 gac gac gag aac aag gtg gtg tcg tac agc gtg gtg gac ggc gag ctg         350
Asp Asp Glu Asn Lys Val Val Ser Tyr Ser Val Val Asp Gly Glu Leu
                 80                  85                  90 gcg gac ttc tac aag aac ttc aag atc acg ctg aag gtg act ccg gcc         398
Ala Asp Phe Tyr Lys Asn Phe Lys Ile Thr Leu Lys Val Thr Pro Ala
             95                 100                 105 aag gcg gag ggc gag ggc ggc gcc gtc gtc agc tgg gcc atg gag ttc         446
Lys Ala Glu Gly Glu Gly Gly Ala Val Val Ser Trp Ala Met Glu Phe
        110                 115                 120 gac aag gcc aac gac cag gtg cct gac ccg gac gtc atc aag gag acc         494
Asp Lys Ala Asn Asp Gln Val Pro Asp Pro Asp Val Ile Lys Glu Thr
    125                 130                 135 gcc acc aag acg ttc cac gac ctc gac gac tac ctc ctc aag aac tag         542
Ala Thr Lys Thr Phe His Asp Leu Asp Asp Tyr Leu Leu Lys Asn *
140                 145                 150 atggagcgag aactggagat ggtccagtac agtacagttc cagtccattc atcgacgcgt        602
cacagtttac tagtgcacgt cgctggtgtg gtgtggtgcc cgtgctggtt ccttaatttg        662
cttactagct agctacgtac cgcggtccgt gtccttgtct ctggctgatg tttgctgcct        722
gcgtccgtcg tgcatccgac gacgtgtcgt tgcgttgcgc accggtcctc cgagtcaata        782
```

```
aagctctccg tgttcattgc gcatcgcttc gaaccaaaaa aaaaaaaaaa aaa          835
```

```
<210> SEQ ID NO 2
<211> LENGTH: 154
<212> TYPE: PRT
<213> ORGANISM: Zea mays

<400> SEQUENCE: 2

Met Ala Ser Lys Val Glu Leu Val Val Glu Val Lys Ser Pro Ala Asp
 1               5                  10                  15

Lys Leu Trp Ala Ala Leu Arg Asp Ser Thr Glu Leu Phe Pro Lys Ile
            20                  25                  30

Phe Pro Glu Gln Tyr Lys Ser Ile Glu Thr Val Glu Gly Asp Gly Lys
        35                  40                  45

Ser Ala Gly Thr Val Arg Leu Leu Lys Tyr Thr Glu Ala Val Pro Met
    50                  55                  60

Leu Thr Phe Ala Lys Glu Lys Leu Glu Thr Ala Asp Asp Glu Asn Lys
65                  70                  75                  80

Val Val Ser Tyr Ser Val Val Asp Gly Glu Leu Ala Asp Phe Tyr Lys
                85                  90                  95

Asn Phe Lys Ile Thr Leu Lys Val Thr Pro Ala Lys Ala Glu Gly Glu
            100                 105                 110

Gly Gly Ala Val Val Ser Trp Ala Met Glu Phe Asp Lys Ala Asn Asp
        115                 120                 125

Gln Val Pro Asp Pro Asp Val Ile Lys Glu Thr Ala Thr Lys Thr Phe
    130                 135                 140

His Asp Leu Asp Asp Tyr Leu Leu Lys Asn
145                 150
```

```
<210> SEQ ID NO 3
<211> LENGTH: 1030
<212> TYPE: DNA
<213> ORGANISM: Zea mays

<400> SEQUENCE: 3
cttactatag ggcacgcgtg gtcgacggcc cgggctggta tgaaggtggg aacctcactg     60
gatgcatata ctgctgagag ataacatcac aattcacaag cttcgatgtc actacagcct    120
acagccattc cgagcagggc gcttaggacg gccgtcaata acttggagga actgccaaga    180
atgtggatta caacagttct atctgagcga cagtctaaac gcagctttgt atagtcattt    240
ttatctcccc aaccggcatt agtaagcagg cccccaacgc attcaaattc gatgtaattg    300
tctacttcat tttggttcag atttgaacga tgtcagtttc aatccacatg caacagaatc    360
cgcagaagaa ttcatccaat tcacacataa agcagcaaca gaagttaaac cataaacatc    420
caattaacga gttgcatttt agatcttta gagaggacaa cctgggctgc agacgagaca    480
aattcggcat caacaacctt ttcgcgcaca agtaatgttt gggtaggcct gaaccgctcg    540
ctattgcagt tggggttggg tggcacccga tgatgtccc atccgaactt gtctccaact    600
ctgcattttc ggttcagagc agtactgcat tttgccattg tcgcctgcac gagagactcg    660
ttactgttcc ggccggaacc ggacctccct cctgctgctg ccaactgcca accagacctg    720
gcatggcctg gtggcgtcat ctaatttctc ctatcaaaga atcacctccc attactccgc    780
cctgtcggc gacctcgtgc cctcgaattc cacgggcaca cggtgcaggc acaccaccgc    840
catcaaaata cggcctcttt gcggcacgga tctgcaccga cgggcgcaat tgaattcgag    900
```

```
cctgatcgag gtggttggat cgcgcaggga aaccttgaat ggccggcatc agtagcaccg      960
gcacgtcacc tctgaagaag agctgtcgcg gtctgagatg tcgctggctc tgtatatata     1020
caaggtctgg                                                            1030
```